United States Patent [19]

Ekwall et al.

[11] 4,388,928
[45] Jun. 21, 1983

[54] SIGNAL PROCESSING MEANS PARTICULARLY FOR HEART PACEMAKERS

[75] Inventors: Christer Ekwall, Solna; Håkan Elmqvist, Bromma, both of Sweden

[73] Assignee: Siemens Aktiengesellschaft, Berlin & Munich, Fed. Rep. of Germany

[21] Appl. No.: 190,221

[22] Filed: Sep. 24, 1980

[30] Foreign Application Priority Data

Sep. 27, 1979 [DE] Fed. Rep. of Germany ....... 2939197

[51] Int. Cl.³ ............................................. A61N 1/36
[52] U.S. Cl. ............................................. 128/419 PG
[58] Field of Search ................................. 128/419 PG

[56] References Cited

U.S. PATENT DOCUMENTS 4,203,447 5/1980 Keller, Jr. et al. ........... 128/419 PG
4,211,235 7/1980 Keller, Jr. et al. ........... 128/419 PG

FOREIGN PATENT DOCUMENTS 2826189 1/1979 Fed. Rep. of Germany ...... 128/419 PG

Primary Examiner—William E. Kamm
Attorney, Agent, or Firm—Hill, Van Santen, Steadman, Chiara & Simpson

[57] ABSTRACT

The exemplary embodiment comprising a signal reception part and a routing device which routes specific signal information for storage to information memories provided for that purpose. The goal of the disclosure is to create such a signal processing means which, given the lowest possible circuit-technical outlay, always prevents an undesired re-programming of information memories with absolute certainty. This goal is inventively achieved in that a locking register is allocated to a memory bank constructed of a plurality of information memories, in which locking register a locking signal can be inscribed for each information memory which is specifically allocated to this information memory, on the basis of which locking signal a change of the stored informational content is made impossible as long as no opening signal for an appertaining information memory is input into the locking register from the outside.

5 Claims, 1 Drawing Figure

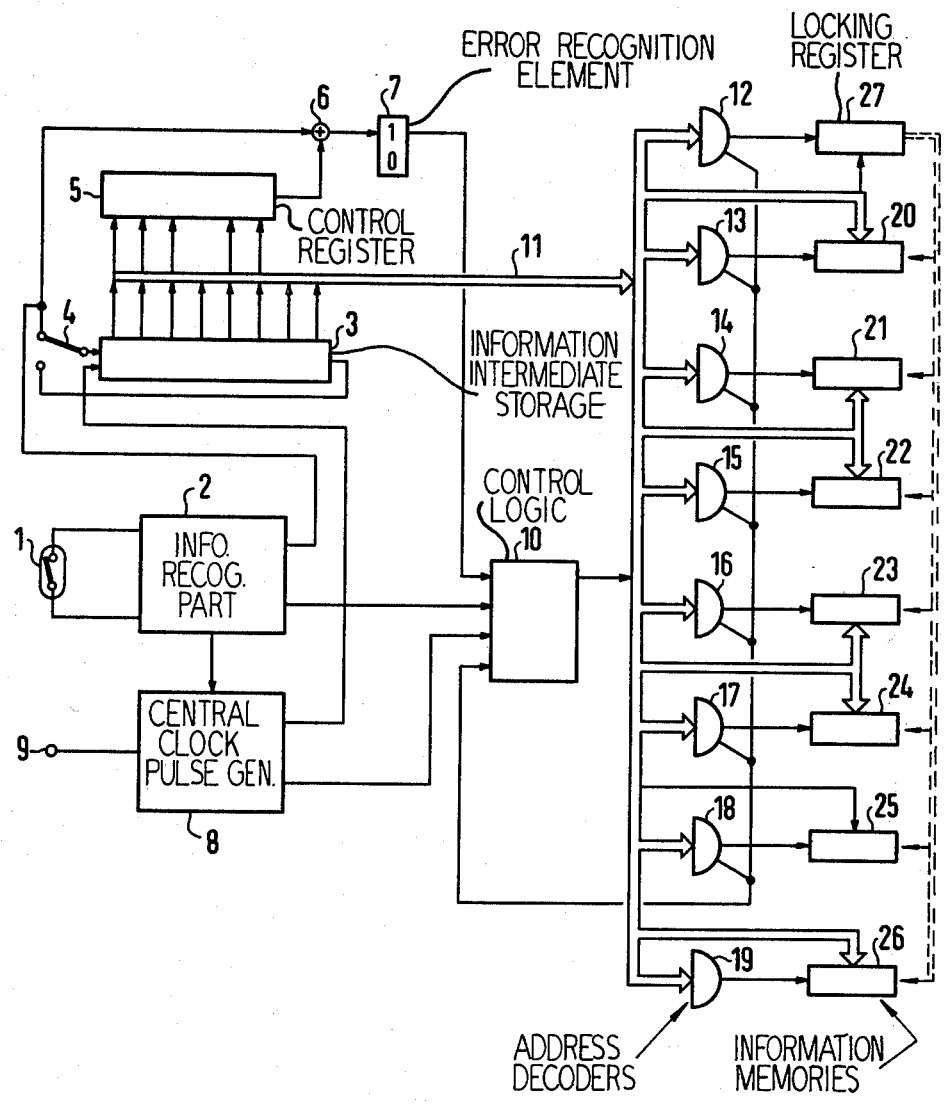

SIGNAL PROCESSING MEANS PARTICULARLY FOR HEART PACEMAKERS

BACKGROUND OF THE INVENTION

The invention relates to a signal processing means, particularly for heart pacemakers, comprising a signal reception part and a routing device which routes specific signal information for storage in data memories provided for that purpose.

Signal processing means of this type, particularly for use in heart pacemakers, should exhibit a plurality of information memories which can be individually inscribed with signal information such as frequency, amplitude course, hysteresis, etc. In general, this inscription ensues in such manner that all necessary information concerning the pacemaker signal to be employed is input by means of a suitable program generator from the outside, i.e. through the skin, for routing into the information memories. In practice, this assumes the aspect that all new information is prescribed by the physician and is finally also input programwise by said physician. In the normal case, the patient himself can then exercise no influence on the input information. In contrast to this standard employment, however, there is often a desire that a subsequent regulation of the information, at least given very specific information, should also be possible by the patient to a limited degree. For example, it should be possible that a specific information should be changeable by the patient within certain limits in accord with the different demands of the daily rhythm. The provision of such a possibility of change by the patient, however, presumes that measures are undertaken that see to it that only the admissable magnitude not, however, other information already inscribed can be changed by the patient.

SUMMARY OF THE INVENTION

The object of the present invention is to create a signal processing means, particularly for employment in heart pacemakers, which, given the lowest possible circuit-technical outlay, always prevents an undesired re-programming with absolute certainty.

The object is inventively achieved in that a locking register is allocated to a memory bank constructed of a plurality of information memories, into which locking register a specific locking signal allocated to each information memory can be inscribed, due to which a change of the stored informational content is made impossible as long as an opening signal for the appertaining information memory is not input from the outside into the locking register.

Further advantages and details of the invention derive from the following description of an exemplary embodiment on the basis of the accompanying drawing sheet in conjunction with the subclaims; and other objects, features and advantages will be apparent from this detailed disclosure and from the appended claims.

BRIEF DESCRIPTION OF THE DRAWINGS

The single FIGURE shows the invention by means of a basic circuit diagram.

DETAILED DESCRIPTION

In the FIGURE, a circuit closer (a magnetically controlled reed contact) for inputting signal information into a signal reception part 2 through 9 of an implantable heart pacemaker is referenced with 1. The switch 1 is actuatable from the outside, i.e. through the skin of the pacemaker patient. The signal reception part comprises an information recognition part 2, an information intermediate storage 3 (shift register) with a change-over 4, as well as a control register 5 with a comparison element 6 and an error recognition element 7. A central clock pulse generator is referenced with 8. It is charged with basic clock pulse impulses at an input 9. Insofar as the error control has not produced an error, the data registered by the information intermediate memory 3 controlled by a control logic 10, are routed to a bank of information memories 20 through 26 via an information line 11 and via address decoders 12 through 19. The individual information memories are constructed in such manner and are driven in such manner that each memory separately carries a specific information allocated to the heart pacemaker signal. Thus, for example, the information memory 20 carries the information concerning the frequency of the heart pacemaker pulses, whereas the information memory 22 carries the information concerning pulse duration and the information memory 23 carries the information concerning hysteresis. The information memory 24 contains the amplitude information, whereas the memories 25 and 26, for example, can be exploited for storing information which relate to the stimulus threshold of the heart and which can be gained, for example, according to the vario principle (step-by-step reduction of the heart pacemaker amplitude until the stimulus threshold is reached). The information memory 21 can serve as a reserve memory.

The essence of the invention, now, is that a locking register 27 is allocated to all of these memories. This locking register 27 is controllable from the outside and contains locking information on the basis of which a change of the stored informational content for each of the individual information memories 20 through 26 is made impossible as long as an opening signal for an appertaining information memory is not input into the locking register from the outside. In the present exemplary embodiment, the locking register is a matter of such a one as contains a two bit information storage location for each individual memory 20 through 26. Insofar as the register 27 carries a not information (e.g. ZERO, binary) in the registered location specifically assigned to an information memory 20 through 26 the appertaining information memory is inaccessible for any type of change of the stored information. If, however, the appertaining register location is in a yes formation (e.g. ONE, binary), then the possibility of changing an inscribed information in the appertaining information memory by means of influence from the outside exists.

In practice, thus, all information for the individual information memories 20 through 26 are usually input by the physician. In some specific cases, there will be no necessity to change the information once input, at least for a certain time span. Accordingly, the physician can also input a locking signal for all information for the individual memories into the locking register 27 at the same time as he inputs the information. In other cases, occasional information correction in accord with the patient's need will be necessary and desirable (for example, for adapting individual information to the altered daily rhythm). In order that such an information correction can be undertaken by the patient himself, the physician will admit a possibility of variation for the patient, specifically only for this information in this specific information memory, by means of inputting a special opening signal into the locking register 27. The locking signal once input remains for all other information memories in which the information once input is to be unchangeable. An example of a rather frequent use is that the pacemaker frequency should be changeable over the course of the day. In this case, thus, the physician will provide a locking signal in the locking register 27 for all information memories except the information memory 20 for the frequency. An opening signal is programmed in the locking register only for the information memory 20. On the basis of this opening signal, then the patient can undertake a frequency correction adapted to his altered need at any time in the course of the day. Thus, given the lowest possible circuit-technical outlay, a possibility is created for easily undertaking re-programmings of a desired type, whereas those of an undesired type are, at the same time, always prevented with absolute certainty.

It will be apparent that many modifications and variations may be effected without departing from the scope of the novel concepts and teachings of the present invention.

We claim as our invention:

1. Signal processing means, particularly for heart pacemakers, comprising a signal reception part and a routing device connected with said signal reception part which routes specific signal information for storage,
    (a) a memory bank having information memories connected with said routing device and operative for receiving respective types of signal information; and
    (b) a locking register (27) allocated to the memory bank and individually controlling enablement of said information memories (20 through 26), into which locking register (27) a locking signal can be inscribed for each information memory which is specifically assigned to said information memory, and on the basis of which a change of the stored informational content is made impossible as long as an opening signal for an appertaining information memory is not input into the locking register (27) from the outside;
    (c) said information memories (20 through 26) having respective information inputs connected in common with said signal reception part for receiving signal information therefrom, and each having a respective individual control input for selectively enabling a change of the informational content stored by such information memory, and each having an address decoder means as part of said routing device for determining which information memory is intended to receive signal information supplied to the information inputs from the signal reception part; and
    (d) said locking register (27) being connected with and controlling the control input of each of said information memories (20 through 26) and individually controlling the enablement of said information memories (20 through 26) for locking selected individual information memories against a change of stored informational content by means of respective individual locking signals being inscribed in said locking register (27) with respect thereto, and for enabling a change of stored informational content of only a selected individual one of said information memories by means of said opening signal therefor.

2. Signal processing means according to claim 1, characterized in that the locking register (27) contains register locations for locking or opening signals separately allocated to the individual information memories (20 through 26).

3. Signal processing means according to claim 1, characterized in that the locking register has two bit information storage means for the respective information memories of which the not information corresponds to the locking signal and the yes information corresponds to the opening signal.

4. Signal processing means according to claim 1, characterized in that programming devices are allocated, of which one is for specific servicing, for example, by the physician, rendering possible any desired programming of the individual information memories (20 through 26) given simultaneous input of desired information signals for the locking registers (27).

5. Signal processing means according to claim 4, characterized in that a further programming device is designed in such manner that it only allows a re-programming of the locking register (27) to a limited degree in response to opening signals for specific, individual information memories whose re-programming is to be made possible.

* * * * *